United States Patent
Cherkassky

(10) Patent No.: US 9,844,228 B2
(45) Date of Patent: Dec. 19, 2017

(54) SPRAY METHOD AND COMPOSITION FOR REDUCING PSYCHOLOGICAL HUNGER

(71) Applicant: Michael Cherkassky, Fort Worth, TX (US)

(72) Inventor: Michael Cherkassky, Fort Worth, TX (US)

(73) Assignee: Michael Cherkassky, Fort Worth, TX (US)

( * ) Notice: Subject to any disclaimer, the term of this patent is extended or adjusted under 35 U.S.C. 154(b) by 0 days.

(21) Appl. No.: 14/336,271

(22) Filed: Jul. 21, 2014

(65) Prior Publication Data

US 2014/0335222 A1    Nov. 13, 2014

Related U.S. Application Data

(63) Continuation-in-part of application No. 14/047,420, filed on Oct. 7, 2013, now abandoned, which is a continuation-in-part of application No. 13/571,399, filed on Aug. 10, 2012, now abandoned.

(51) Int. Cl.

| | |
|---|---|
| *A61K 36/54* | (2006.01) |
| *A61K 36/752* | (2006.01) |
| *A61K 36/00* | (2006.01) |
| *A23L 33/00* | (2016.01) |
| *A61K 9/00* | (2006.01) |

(52) U.S. Cl.
CPC .............. *A23L 33/30* (2016.08); *A61K 9/006* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 5,087,458 A | 2/1992 | Witkewitz et al. | |
| 6,086,888 A | 7/2000 | Belgorod | |
| 2005/0112149 A1 | 5/2005 | Belote et al. | |
| 2006/0292254 A1 | 12/2006 | More | |
| 2010/0016210 A1 | 1/2010 | Cherkassky | |
| 2012/0156272 A1* | 6/2012 | Rebmann | 424/401 |

FOREIGN PATENT DOCUMENTS

| | | | |
|---|---|---|---|
| EP | 0267735 A2 * | 5/1988 | |
| WO | WO 2008005548 A3 | 1/2008 | |

OTHER PUBLICATIONS

Friedman et al. (1976) Psychological Reviews, vol. 83, No. 6, 409-431.*
Alsio et al. (2012) Frontiers in Neuroendocrinology 33, 127-139.*
Avena et al. (2012) Nutrition 28, 341-343.*
Halford et al. (2011) Drugs, 71(17): 2247-2255.*
Meredith, K. (2000) Transactional Analysis Journal, vol. 30, No. 4, 285-291.*
Mithieux, G. (2013) Trends in Endocrinology and Metabolism, vol. 24, No. 8, 378-384.*
Raskin et al. (2004) Current Phamaceutical Design, 10, 3419-3429.*
Website document entitled: "Creamy Cinnamon Vanilla Coffee" (available at http://www.food.com/recipe/creamy-cinnamon-vanilla-coffee-346903). Downloaded from website: Jul. 8, 2015.*
Website document entitled: "Lemon Powder" (available at http://www.liveandfeel.com/articles/lemon-powder-2980). Downloaded from website: Jul. 8, 2015.*
Revilla et al. (1998) J. Agric. Food Chem. 46, 4592-4597.*
Cichewicz et al. (1996), The antimicrobial properties of chile peppers (*Capsicum* species) and their uses in Mayan medicine, J. Ethnopharm. 52:61-70.
Kozukue et al. (2005), Analysis of eight capsaicinoids in peppers and pepper-containing foods by high performance . . . , J. Agric. Food Chem. 53:9172-9181.
Westerterp-Plantenga et al. (2005) Sensory and gastrointestinal satiety effects of capsaicin on food intake, Internat. J. of Obesity 29:682-688.
Westertep-Plantenga et al. (2006), Metabolic effects of spices, teas, and caffeine, Physiol. & Behavior 89:85-91.
Aher et al. (2009), Novel pepper extract for enhanced P-glycoprotein inhibition, J. Pharmacy and Pharmacology 61:1179-1186.
Mishra et al. (2010), Effect of capsaicin on satiety and diet-induced thermogenesis, Proc. Nutrition Society of New Zealand 1-6.
McRobbie et al. (2010), A randomised trial of the effects of two novel nicotine replacement therapies on tobacco withdrawal . . . , Addiction 105:1290-1298.

(Continued)

*Primary Examiner* — Chris R Tate
*Assistant Examiner* — Russell Fiebig
(74) *Attorney, Agent, or Firm* — Eldredge Law Firm; Richard Eldredge

(57) ABSTRACT

A spray composition and method are provided that are effective for reduction or elimination of the psychological hunger for foods for which a patient wishes to reduce consumption. Such ingredients preferably include but are not limited to cinnamon, lemon powder, coffee grounds, alcohol, citric acid, vanilla, and sugar and/or an artificial sweetener such as saccharin. The composition of the invention is preferably sprayed into the mouth, resulting in a lessening or elimination of psychological hunger. The method and spray composition saturate a person's craving for foods by penetrating to the blood through the oral mucosa, and satisfying taste buds.

2 Claims, No Drawings

(56) References Cited

OTHER PUBLICATIONS

Ludy et al. (2012), The effects of capsaicin and capsiate on energy balance: critical review and meta-analyses of studies in humans, Chem. Senses 37:103-121.
Website entitled "Sprayology Diet Power" (available at http://www.altmednetwor.net/sprayoloyg_dietpowr.html); downloaded by patent examiner on Feb. 12, 2013.

* cited by examiner

SPRAY METHOD AND COMPOSITION FOR REDUCING PSYCHOLOGICAL HUNGER

CROSS-REFERENCE TO RELATED APPLICATIONS

This application is a continuation-in-part of copending application Ser. No. 14/047,420 filed Oct. 7, 2013, which is a continuation-in-part application of Ser. No. 13/571,399 filed Aug. 10, 2012, now abandoned.

BACKGROUND OF THE INVENTION

Field of the Invention

This invention relates to preparations that reduce psychological hunger for food substances and other substances that are orally consumed or otherwise orally provided, such as the smoking of tobacco. In particular the invention relates to spray preparations and a method for reducing psychological hunger.

Description of the Related Art

There are many physical reasons why people crave food, the most basic of which is actual hunger and stomach pangs because of lack of eating often enough and insufficient food consumption. For persons who have eaten sufficiently however, there are also often feelings of the need to eat that can be termed "psychological hunger". Psychological hunger generally occurs when people are bored, and their thoughts turn to food and they eat because it is something to do and is interesting. Psychological hunger also can occur when people are feeling stress, and they feel that their stress can be relieved by eating.

Excessive eating when people are bored or under stress can result in increases in weight, which can become a major problem, especially when they are already overweight or obese. Further, their excessive weight can cause them stress, causing them to eat more and exacerbating the problem. Even when people are on weight loss diets and are able to regulate their eating at mealtimes, psychological stress can cause them to eat more than their diet allows, particularly between meals if they are bored or under stress.

Today obesity is one of the most serious health problems in the United States, with approximately 30% of adults suffering from obesity, and at least 50% of adults in the United States being overweight. The problem of obesity in the United States and most western countries has been steadily increasing in the last several decades. Such obesity has caused or contributed to a marked increase in the occurrence of heart diseases, hypertension, diabetes, arthritis and increased morbidity and mortality. There is also recent research which links obesity with different types of cancer, particularly breast cancer. Obesity is a serious public health hazard, second in importance only to tobacco. Being overweight reduces lifespan as well as quality of life.

There are many methods suggested for management of obesity and overweight. These include diets that exclude fats and high caloric elements, appetite suppressants, psychotherapeutic techniques and operative techniques. One of the most common methods is the use of stimulants. Amphetamine-like agents act on the brain to reduce the sensation of hunger. Experience indicates that most of the appetite suppressants work for a short period of time, but a few weeks or a few months later they lose most of their potency and patients start regaining weight. There is also a serious problem with the maintenance of a desirable weight after it is achieved, for the simple reason that appetite suppressants cannot be continued indefinitely at full strength.

The reason that most people become overweight is that they consume more nutrition calories than they require, often primarily because of cravings for certain foods, such as chocolate or potato chips. In other words, humans do not only eat to survive, but also eat for the taste, flavor and gratification. The degree of the satiety has changed and is predicated not only the necessary nutritional requirements but also on unphysiological "unnatural" pleasure drive.

The method of Cherkassky (U.S. Pat. No. 8,298,571 B2) provides a product and a treatment method using certain food ingredients in a manner that reduces or eliminates the craving for eating of foods for which the patient wishes to reduce consumption. Such ingredients include but are not limited to margarine, mustard, pepper and salt, preferably applied to the surface of the tongue as a paste, and then the craved substance is administered orally with the paste or with the non-binder components of the paste. Because psychological hunger is often not related to a particular substance craving, there is a need for a composition and method that generally reduces psychological hunger.

Another method of Cherkassky (U.S. Pat. No. 8,323,682) provides a capsular product that preferably contains a cellulose product (preferably METHOCEL E4M 4000™) which has been mixed with ethanol during the preparation of the capsule, and most preferably the capsule also contains a protein product, a spice (e.g., cayenne pepper, mustard), a sweetener (e.g., saccharin), and salt.

The spray method of Cherkassky (co-pending Ser. No. 14/047,420) provides a product and treatment method for reduction or elimination of the psychological hunger for foods for which a patient wishes to reduce consumption, and includes ingredients such as cayenne pepper, alcohol, salt, citric acid and a sweetener such as saccharin, and includes other ingredients that desensitize the taste buds and reduce hunger.

Prior methods (e.g., the method of Belote et al., U.S. Patent Application Publication No. 2005/0112149) operate to diminish the desire for food intake by masking or reducing the flavor of foods and/or anesthetize the taste buds.

There is a need for a method that saturates and satisfies the brain of a person by penetrating to the blood through the oral mucosa, and satisfying taste buds.

It is therefore an object of the invention herein to provide a spray composition and method that not only reduces psychological hunger without being targeted toward any particular food cravings, and reduces hunger through oral mucosa penetration and satisfies taste buds with an essentially instantaneous result.

It is an object of the invention herein to provide a non-toxic method and composition for reducing or eliminating psychological hunger without side effects.

It is an object of the invention herein to provide a spray composition and method that can be easily used to reduce psychological hunger.

Other objects and advantages will be more fully apparent from the following disclosure and appended claims.

SUMMARY OF THE INVENTION

The invention herein is a spray composition and method effective for reduction or elimination of the psychological hunger for foods for which a patient wishes to reduce consumption, and alternatively, for tobacco. The method and spray composition saturate a person's craving for foods by penetrating to the blood through the oral mucosa, and satisfying taste buds.

The ingredients used in the invention herein preferably include but are not limited to cinnamon, lemon powder, coffee grounds, alcohol (such as brandy), citric acid, a sweetener such as saccharin and/or sugar and vanilla extract. The composition of the invention is preferably sprayed into the mouth, resulting in a lessening or elimination of psychological hunger through penetration of the components to the blood through the oral mucosa, and satisfying taste buds.

Other objects and features of the inventions will be more fully apparent from the following disclosure and appended claims.

DETAILED DESCRIPTION OF THE INVENTION AND PREFERRED EMBODIMENTS THEREOF

The present invention in its preferred embodiment includes the administration of a liquid composition of the invention in the form of a spray to humans. The preferred composition of the invention includes cinnamon, more specifically, *cinnamomum verum*, lemon powder, ground coffee, alcohol, citric acid, and saccharin (non-caloric sweetener) and/or sugar. In addition the composition of the invention herein includes vanilla extract. Spraying the liquid composition into the mouth of the person causes reduction of psychological hunger within 10-15 seconds because of penetration of the composition through the oral mucosa, and satisfying taste buds.

The composition of the invention is administered by spraying into the mouth as discussed herein.

The proportion of ingredients can vary, and additional ingredients may be included.

The composition of the invention is preferably prepared by mixing the ingredients to form a sprayable liquid.

In addition, the composition of the invention herein for reducing psychological hunger can be combined with currently commercially available or future preparations without detrimental effect because of the lack of side effects of the invention herein.

Administration of the invention therefore is in the form of spraying a liquid into the mouth of a person that suffers from psychological hunger, such as may be due to boredom or stress.

As an added benefit of this type of administration according to the invention, patients who smoke may further be caused to cease or reduce smoking by encouraging the patient to spray the composition of the invention into the mouth.

While the invention herein may be used without other products, it is also contemplated that the invention herein may be administered to the patient with the appetite suppressant product and using the method disclosed in U.S. Pat. No. 8,323,682 of the Applicant herein, in which a capsular product is administered that preferably contains a cellulose product (preferably METHOCEL E4M 4000™) which has been mixed with ethanol during the preparation of the capsule, and most preferably the capsule also contains a protein product, a spice (e.g., cayenne pepper, mustard), a sweetener (e.g., saccharin), and salt.

Alternatively, or in addition the invention herein may be administered to the patient and with the product for substance craving using the method disclosed in U.S. Pat. No. 8,298,571 of the Applicant herein, in which ingredients including but not limited to margarine, mustard, pepper and table salt, are applied to the surface of the tongue as a paste, and then the craved substance is administered orally with the paste or with the non-binder components of the paste The features of the present invention will be more clearly understood by reference to the following examples, which are not to be construed as limiting the invention.

Example 1

Preparation of Composition of the Invention

The method of preparation of the composition of the invention herein is preferably as follows:
1. Prepare a mixture of equal parts dried ground cinnamon, lemon powder (dried lemon) and coffee grounds. Add 1 part of the mixture to 10 parts alcohol (1:10) and allow to sit covered at room temperature for approximately a week. The alcohol may be any consumable, non-toxic alcohol, such as ethanol or brandy and the like.
2. Remove sediment from the alcohol mixture, preferably by filtering four times through standard filter paper as known in the art.
3. Mix in 15%-40% by volume of an alcoholic beverage (such as brandy) (or about 7% alcohol if pure alcohol is used), about 0.055% by volume of sugar, about 0.75% by volume of citric acid, and about 0.065% by volume saccharin (or other non-caloric sweetener). While use of both sugar and saccharin is preferred, they may be used interchangeably.
4. Add 1000 cc isotonic salt solution (physiological saline); alternatively water may be used.
5. Add about 30% by volume of vanilla extract (standard, off-the-shelf, as known in the art).

While the concentrations provide above are preferred, variations in the concentrations of the components can be made without causing the composition to be ineffective.

The composition of the invention is preferably stored at room temperature.

Example 2

Use of the Composition of the Invention

The composition of the invention according to Example 1 is placed in a spray bottle for individual use. Persons desiring to reduce psychological hunger that may be caused by boredom or stress or other causes spray a few puffs (e.g. 2-4 puffs) of the composition of the invention into their mouths at any time of the day. There is immediate relief from the psychological hunger, which is decreased or eliminated completely. If the hunger is truly psychological hunger (and not physical hunger), such an administration of the composition of the invention gives 6-8 hours of relief.

Example 3

Use of the Composition of the Invention with Additional Capsules or Other Product If the person has actual physical hunger and is trying to reduce food consumption, the treatment with the spray is combined with the capsules of Cherkassky (U.S. Pat. No. 8,323,682) or with diet pills as known in the art. Such appetite suppressant product also includes tablets and other formulations known in the art.

Alternatively, or in addition, the spray method of the invention herein is combined with use of the method of Cherkassky (U.S. Pat. No. 8,298,571 B2), which provides a product and a treatment method using certain food ingredients in a manner that reduces or eliminates the craving for eating of foods for which the patient wishes to reduce consumption, including margarine, mustard, pepper and salt, preferably applied to the surface of the tongue as a paste.

The composition may be administered more frequently if desired.

While the invention has been described with reference to specific embodiments, it will be appreciated that numerous variations, modifications, and embodiments are possible, and accordingly, all such variations, modifications, and embodiments are to be regarded as being within the spirit and scope of the invention.

What is claimed is:

1. A method for reducing a person's craving for a food or tobacco substance comprising spraying into the mouth of a person in need thereof a composition, said composition comprising effective amounts of:
   a. an alcoholic extract containing a mixture of cinnamon, lemon powder, coffee grounds,
   b. vanilla extract;
   c. a sweetener; and
   d. citric acid.

2. The method of claim 1 wherein the liquid composition is prepared by steps comprising:
   a) mixing cinnamon, lemon powder and coffee grounds in equal parts with alcohol to form an extract mixture and allowing the mixture to sit covered;
   b) removing sediment from the mixture resulting in a supernatant liquid;
   c) mixing sweetener, citric acid and vanilla extract with the supernatant liquid; and
   d) adding an aqueous liquid selected from the group consisting of isotonic salt solution and water to the mixture obtained by step c).

* * * * *